United States Patent
Lange

(12)
(10) Patent No.: US 6,692,146 B1
(45) Date of Patent: Feb. 17, 2004

(54) RUBBER HOT-WATER BOTTLE CLOSURE

(76) Inventor: Georg Oswald Lange, Heidelberger Strasse 21, D-28203 Bremen (DE)

(*) Notice: Subject to any disclaimer, the term of this patent is extended or adjusted under 35 U.S.C. 154(b) by 0 days.

(21) Appl. No.: 09/890,197

(22) PCT Filed: Jan. 5, 2000

(86) PCT No.: PCT/EP00/00033

§ 371 (c)(1),
(2), (4) Date: Jan. 22, 2002

(87) PCT Pub. No.: WO00/40187

PCT Pub. Date: Jul. 13, 2000

(30) Foreign Application Priority Data

Jan. 6, 1999 (DE) .......................... 199 00 197

(51) Int. Cl.[7] .............................................. B65D 33/02
(52) U.S. Cl. ............................ 383/34; 383/59; 383/68; 383/901; 383/904
(58) Field of Search ............................ 383/68, 69, 36, 383/34, 34.1, 35, 901, 904, 906, 59

(56) References Cited

U.S. PATENT DOCUMENTS

| | | | | |
|---|---|---|---|---|
| 939,520 A | * | 11/1909 | Leyner ........................ 383/68 |
| 1,183,962 A | * | 5/1916 | Eggers ........................ 383/43 |
| 1,381,067 A | * | 6/1921 | Eguchi ........................ 383/34 |
| 2,055,695 A | * | 9/1936 | MacDonald ................ 383/68 |
| 2,500,363 A | * | 3/1950 | Koeppel ...................... 383/59 |
| 2,544,929 A | * | 3/1951 | Madsen et al. ............. 607/112 |
| 2,622,646 A | * | 12/1952 | Miller .......................... 383/93 |
| 5,074,300 A | * | 12/1991 | Murphy ...................... 607/108 |

FOREIGN PATENT DOCUMENTS

GB          0005307       * of 1898 ................. 383/901

* cited by examiner

*Primary Examiner*—Jes F. Pascua
(74) *Attorney, Agent, or Firm*—McGlew and Tuttle, P.C.

(57) ABSTRACT

Prior-art rubber hot-water bottles have a screw cap, which is arranged directly on the bottle body and forms a rather hard thickening there, which is felt to be irritating when the user is lying on the bottle. Moreover, a screw cap is difficult to use and must be screwed in with a certain force, which also requires corresponding forces for loosening. To avoid these drawbacks, it is proposed according to the present invention that a clamping means (23, 40), by which the bottle neck can be closed, be provided on the bottle neck (21) of the rubber hot-water bottle. Clamping means are simple to use and require only little force for closing. In addition, they can be opened easily and are very flat, so that they are not irritating. Furthermore, the bottle neck (21) may be designed such that the clamping means (23, 40) can be led away from the body of the user.

15 Claims, 4 Drawing Sheets

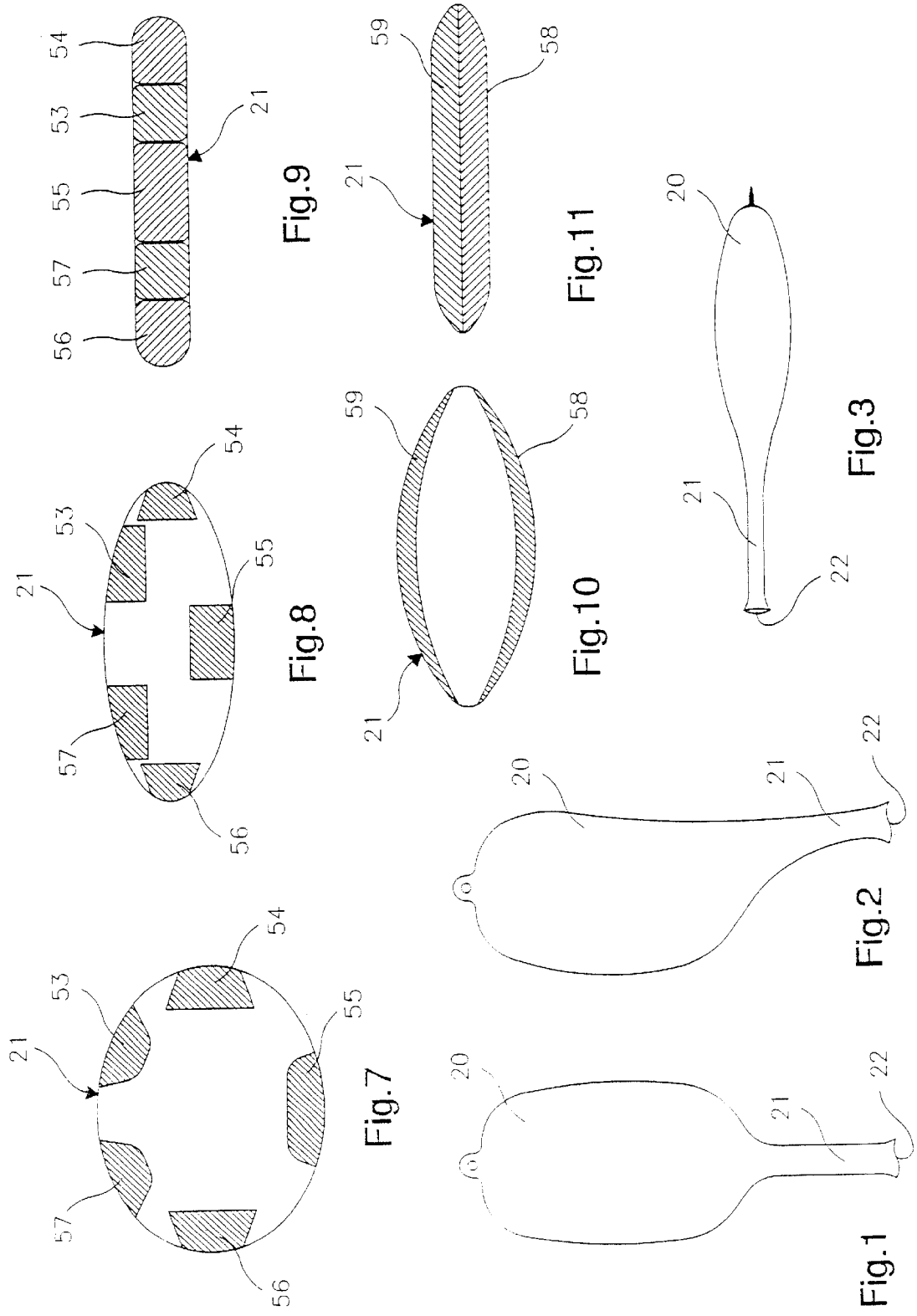

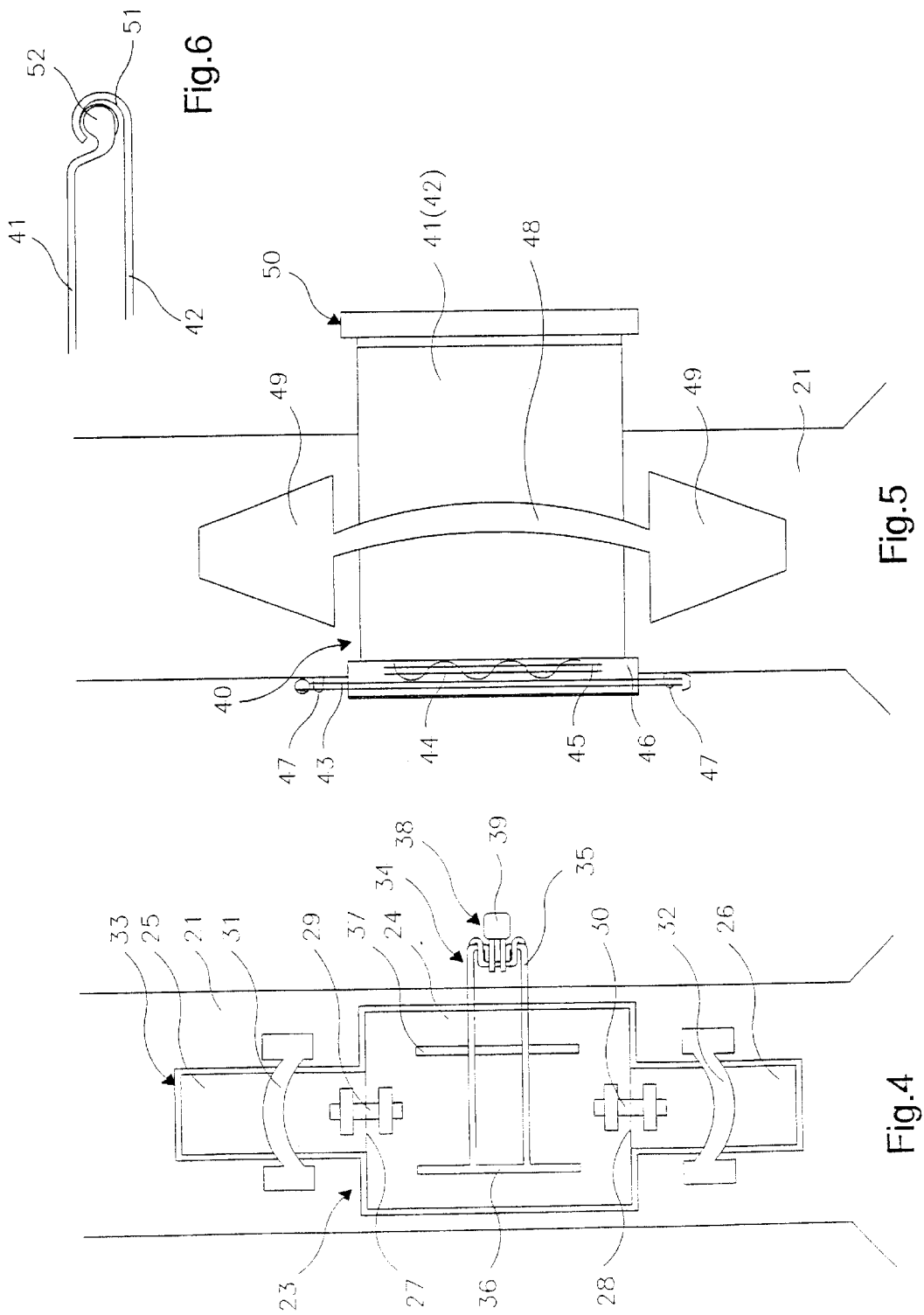

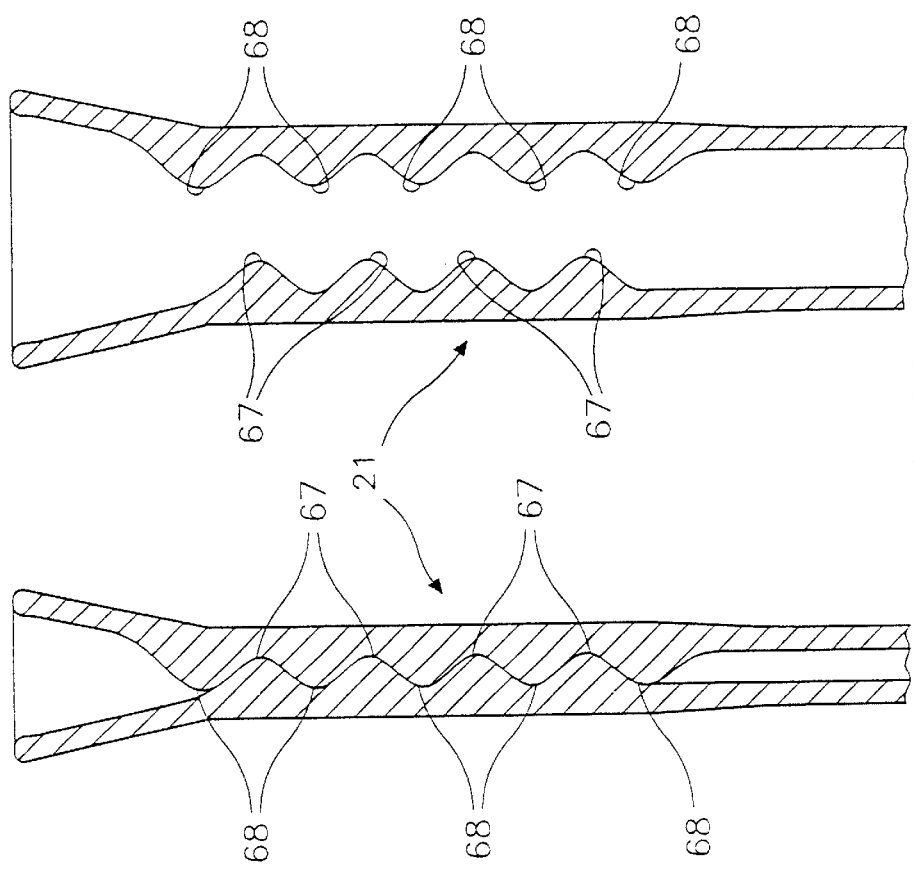
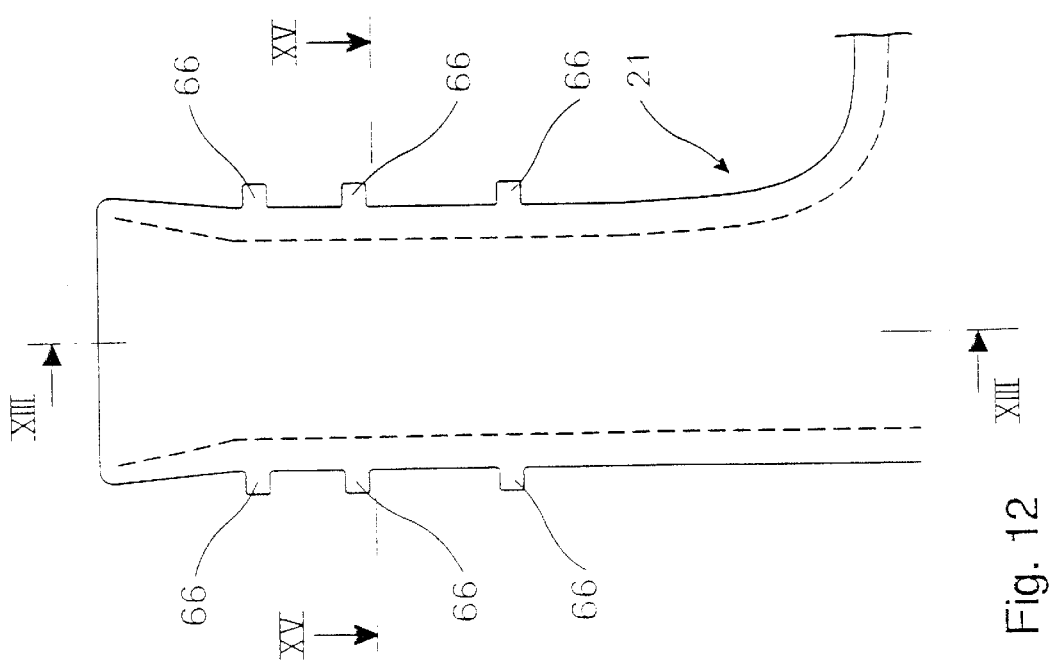
Fig. 14
Fig. 13
Fig. 12

RUBBER HOT-WATER BOTTLE CLOSURE

FIELD OF THE INVENTION

The present invention pertains to a rubber bottle with a bottle body, a bottle neck, which has a filling opening for filling in a hot or cold liquid, especially water, at its free end, and with a closure for closing the filling opening.

BACKGROUND OF THE INVENTION

Such a rubber bottle has been known from, e.g., U.S. Pat. No. 2,500,363, U.S. Pat. No. 2,622,646, U.S. Pat. No. 2,544,929, and GB 141 035. Such rubber bottles are called, in general, hot-water bottles, even though they may just as well also be filled with cold water and thus be used to cool an area of the body. These prior-art rubber hot-water bottles have a very short, hardly perceptible bottle neck, whose filling opening is closed by means of a clamping closure. The drawback of this prior-art rubber hot-water bottle is above all that the clamping closure forms a thickening and is arranged close to the body of the bottle. The closure is therefore felt by the user to be disturbing when he is lying on the bottle. Furthermore, it is disadvantageous that the rubber hot-water bottles must be grasped directly at the neck of the bottle for filling in the hot water. As a result, there is a risk that the user may, e.g., scald himself with splash water. Furthermore, residual air can be removed from the bottle with difficulty only in the case of the prior-art rubber hot-water bottle.

DE-PS 480 921 shows a rubber hot-water bottle, in which a long neck is folded back onto itself several times. The bottle is closed securely as a result. A similar principle is shown in DE-PS 474 443. The drawback of this is the cumbersome and complicated closing of the bottle and the hard thickening caused by the packet of the folded neck directly at the edge of the body of the bottle. This design is therefore very similar to the rubber hot-water bottle used generally.

DE 297 00 310 U1 describes a belt-like rubber hot-water bottle, which can also be worn during sitting or walking. The drawback of this design is that hot water is also present, e.g., in the belts, where it has no benefit and is rather disadvantageous.

The rubber hot-water bottles shown in WO 91/06269 with a special shape are suitable mainly for the special forms of application shown.

Based on this, the basic object of the present invention is to improve a rubber bottle of the type mentioned in the introduction such that the closure is not disturbing when the user is lying, e.g., with his back on the bottle.

SUMMARY AND OBJECTS OF THE INVENTION

To accomplish this object, the rubber bottle according to the present invention is characterized in that the neck of the bottle is designed as a long tube, such that the closure is located at such a spaced location from the body of the bottle when the filling opening is closed that the closure is not located under the user's body during the use of the rubber bottle.

Due to the fact that the closure is located at a markedly spaced location from the body of the bottle because of the long, tubular bottle neck, the closure is no longer located under the user, but is led away from him. The closure is thus not disturbing any longer. During filling, the bottle neck of a rubber bottle, which first lies on a substrate, is raised, and the rubber bottle is filled up to the point of attachment of the bottle neck, i.e., the body of the bottle is filled to the brim. All the air present is now displaced from the body of the bottle without the rubber bottle overflowing, because the neck of the bottle is still available quasi as a reserve. If the user raises a rubber bottle that had been filled excessively somewhat higher, the excess water enters the body of the bottle because the volume of the stretchable rubber bottle, more precisely the volume of the body of the bottle, increases due to the force of gravity. Residual air in the body of the bottle, on the one hand, and overflowing of the rubber bottle during filling, on the other hand, are avoided with certainty as a result, which was not possible in conventional rubber bottles.

Furthermore, all prior-art embodiments have in common the drawback that the bottle must be grasped for filling directly at the neck of the bottle, which entails the above-described risk of scalding. According to a variant, a clamping means for closing the neck of the bottle is arranged on the neck of the bottle. The clamping means has corresponding clamping jaws, between which the neck of the bottle can be clamped. The clamping jaws are used in the opened position as a grip for grasping the rubber bottle during filling. Thus, the rubber bottle does not need to be grasped directly by the neck of the bottle any longer, but it has a separate grip in the clamping means. The risk of scalding is thus avoided with certainty.

The clamping means itself is detachably connected to the neck of the bottle by suitable means and it can thus be removed from the neck of the bottle for cleaning purposes. Separate disposal of the clamping means and the rubber bottle, e.g., for recycling, is also possible. For example, hand straps may be used to detachably fasten the clamping means to the neck of the bottle.

According to another embodiment of the present invention, means are provided by which a force is applied to the neck of the bottle for opening the filling opening during the filling with the clamping means opened. Consequently, the filling opening of the rubber bottle is automatically opened by the clamping means in the opened position of the said clamping means, so that the bottle can be filled reliably and easily due to this measure as well. According to a first embodiment, the means for opening are the hand straps, by which the clamping means is held on the neck of the bottle such that the neck of the bottle opens in the spread-apart position of the clamping means. Tongues of the clamping means, which can be inserted into the hand straps to attach the clamping means, may be provided. According to another, alternative embodiment, the means for opening the filling opening are designed such that a pressure is applied to the neck of the bottle at right angles to the closing pressure in the opened position of the clamping means, so that the neck of the bottle opens for filling with the clamping means opened.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a top view of a rubber hot-water bottle;

FIG. 2 is a top view of a modified rubber hot-water bottle;

FIG. 3 is a side view of a rubber hot-water bottle;

FIG. 4 is a schematic view of the bottle neck of a first embodiment of a rubber hot-water bottle having the features of the present invention;

FIG. 5 is a schematic view of the bottle neck of another embodiment of a rubber hot-water bottle having the features of the present invention;

FIG. 6 is a detail view of the closure of a rubber hot-water bottle according to FIG. 5;

FIG. 7 is a cross sectional view of the neck of a rubber hot-water bottle according to FIG. 4 or FIG. 5 in the widely opened position;

FIG. 8 is a cross sectional view of the bottle neck according to FIG. 7 in the resting position;

FIG. 9 is a cross sectional view of the bottle neck according to FIG. 7 in the closed position;

FIG. 10 is a cross sectional view of another bottle neck for a rubber hot-water bottle according to FIG. 4 or 5 in the resting position;

FIG. 11 is a cross sectional view of the bottle neck according to FIG. 10 in the closed position;

FIG. 12 is a schematic view of a bottle neck of a further embodiment of the invention in side view;

FIG. 13 is a cross sectional view of the profile of the bottle neck according to with FIG. 12 through section XIII—XIII in a closed position;

FIG. 14 is a cross sectional view of the profile of the bottle neck according to with FIG. 12 through section XIII—XIII in a opened position;

DESCRIPTION OF THE PREFERRED EMBODIMENT

Figure 15:
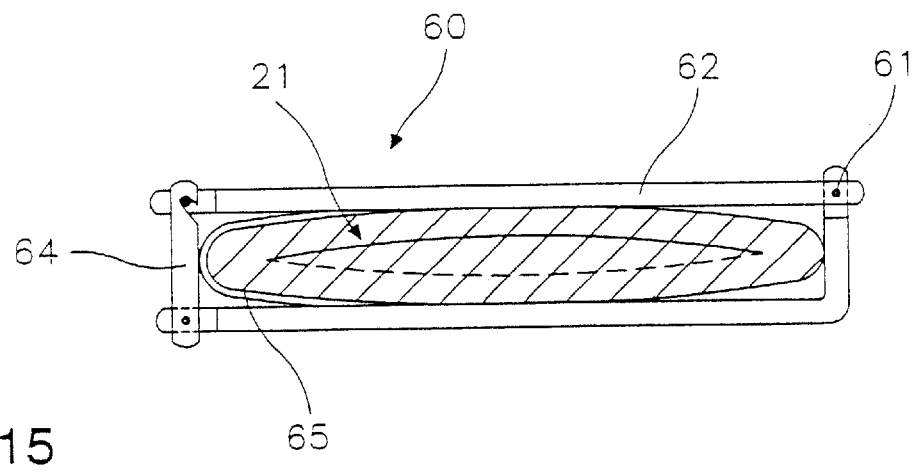
FIG. 15 is a cross sectional view of the bottle neck according to FIG. 12 through section XV—XV in a closed position.
Figure 16:
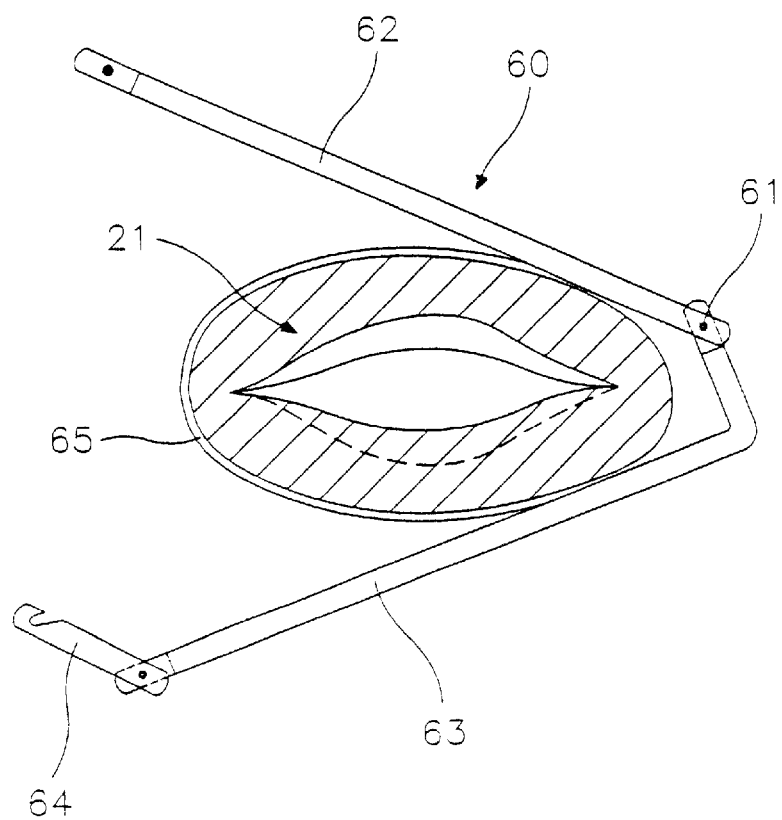
FIG. 16 is a cross sectional view of the bottle neck according to FIG. 12 through section XV—XV in a opened position.

Referring to the drawings in particular, FIGS. 1 through 3 show a rubber hot-water bottle with a bottle body 20 and a relatively marked bottle neck 21. At its free end, the bottle neck 21 has a filling opening 22, through which the rubber hot-water bottle can be filled, usually with hot water, but also with cold water. The bottle is, of course, also emptied through the filling opening 22. The embodiments according to FIG. 1 and FIG. 2 differ in that the bottle neck 21 is arranged in the middle in relation to the bottle body 20, as in the prior-art rubber hot-water bottles, while the bottle neck 21 in the embodiment according to FIG. 2 is arranged laterally offset.

A closure for opening and closing such rubber hot-water bottles is arranged at the bottle neck 21 such that it is located at a markedly spaced location from the bottle body 20. The closure itself has a special shape.

Another embodiment of such a closure is shown in greater detail in FIG. 4. The closure comprises a clamping means 23. On both sides of the bottle neck 21, it has a large-surface clamping jaw 24 each. Tongues 25 and 26 are articulated (articulation lines 27 and 28) to the clamping jaws 24 at the top and bottom when viewed in the longitudinal direction of the bottle neck 21. The tongues 25, 26 are prevented by bars 29 and 30 from folding in relation to the clamping jaws 24.

The tongues 25, 26 are led through holding straps 31, 32, by which the tongues 25, 26 and consequently the clamping jaws 24 are held at the bottle neck 21. To put on the clamping means 23, the tongues 25, 26 are folded and introduced through the holding straps 30, 31. The clamping jaws 24 are then pressed against the bottle neck 21, so that the tongues 25, 26 are folded into the plane of the corresponding clamping jaw 24 and the bars 29 and 30 will snap in as a result. The clamping means 23 is thus fixed on the bottle neck 21 and tightly connected to the bottle neck 21, so that the bottle neck 21 is opened in the spread-out position of the clamping jaws 24. To guarantee accurate positioning of the clamping means 23 at the bottle neck 21, a relief-like depression 33 is recessed in the bottle neck 21. This relief-like depression 33 has the shape of a clamping jaw 24 with the tongues 25 and 26 articulated thereto, as can be clearly recognized from FIG. 4.

The clamping jaws 24 are clamped together by a clamp strap 34. The said clamp strap 34 has, in principle, exactly the same design as in the case of a trouser-hanger, in which the legs of the trousers are placed between two clamping jaws and are then held by pressing together the clamping jaws. As in such a trouser-hanger, the present clamp strap 34 also has a linkage 35 made of a stable wire with elastic properties. The linkage 35 is articulated by means of a hinge 36 to each of the clamping jaws 24 and presses abutments 37 arranged at the clamping jaws 24 in the closed state. A closing strap 38, which can be actuated by means of a grip 39 in exactly the same manner as a hook in the said trouser-hanger, is arranged at the free end of the linkage 35. The clamping means 23 is released by folding down the closing strap 38 by means of the grip 39. The linkage 35 can now be swung apart and the clamping jaws 24 are thus opened. The rubber hot-water bottle can now be filled or emptied. For closing, the clamping jaws 24 are pressed together and the closing strap 38 is then swung into the position shown in FIG. 4 by means of the grip 39 and is locked as a result. The bottle neck 21 is compressed and thus closed.

Another clamping means 40 is shown in FIGS. 5 and 6. This clamping means 40 comprises essentially two clamping jaws 41, 42 arranged on both sides of the bottle neck 21. The clamping jaws 41, 42 are articulated to one another by means of a toggle link 43. A spring 44 pretensions the clamping jaws 41, 42 in the spread-out position, i.e., in the opened position. The spring 44 is now held on an axis 45. The spring 44, the axis 45 as well as the toggle link 43 are mounted in a housing 46. The toggle link 43 and thus the entire clamping means 40 is still held by rings 47 arranged at the bottle neck 21.

The clamping jaws 41, 42 are guided at the bottle neck 21 by a holding strap 48, which is in close contact, so that the bottle neck 21 is opened in the spread-out position of the clamping jaws 41, 42. The holding straps 48 are fastened to the bottle neck 21 by straps 49, e.g., by vulcanization.

At its free end 50 facing away from the toggle link 43, one of the clamping jaws 42 has an end piece 51 bent over in a hook-shaped manner. The other clamping jaw 41 is provided with a corresponding bead 52. By pressing the clamping jaws 41 and 42 against each other, the bead 52 snaps into the hook-like end piece 51 and the clamping means 40 is closed. The bottle neck 21 is pressed together as a result and also closed. For opening, the bead 52 can be removed from the hook-like end piece 51 by the user. The hook-like end piece 51 is provided with elastic properties for closing and for opening alike.

The common feature of the above-mentioned two embodiments of the clamping means 23 and 40 is that the clamping means 23, 40 can be used at the same time as a grip for grasping the rubber hot-water bottle for filling. In the case of the clamping means 23, the rubber hot-water bottle can be grasped by the linkage 35 and, in the case of the clamping means 40, it can be grasped by one of the clamping jaws 41, 42. Furthermore, the two embodiments have corresponding clamping jaws 24; 41, 42, which are provided with large clamping surfaces and require only a weak clamping force. The clamping means 23 and 40 are correspondingly easy to operate, because likewise only weak forces are directed against the clamping or closing force, because these forces act laterally in relation to the said clamping or closing force.

Both embodiments of the clamping means 23, 40 are provided with securing means, not specifically shown, against unintended or spontaneous opening.

However, the bottle neck 21 itself also has a special design, as is shown more specifically in FIGS. 7 through 9 as well as 10 and 11.

The bottle neck 21 according to FIGS. 7 through 9 has longitudinal ribs 53, 54, 55, 56 and 57 on its inside. These longitudinal ribs 53 . . . 57 extend over the entire length of the bottle neck 21 and are designed such that they engage one another in the closed position (FIG. 9) such that the bottle neck 21 is completely closed. In the opened (filling) position (FIG. 7), the longitudinal ribs 53 . . . 57 protrude into the opened bottle neck 21. As a result, the water being filled in is whirled up within the bottle neck 21 to the extent that air present in the bottle body 20 can always escape unhindered through the bottle neck 21. "Splashing back" of the hot water and thus the risk of scalding to the user are avoided with certainty as a result. It can be recognized from FIG. 7 that, e.g., a real air channel, which guarantees the unhindered escape of the air from the bottle body 20, is formed, e.g., between the longitudinal ribs 53 and 57.

A simpler embodiment for the bottle neck 21 is shown in FIGS. 10 and 11. The bottle neck 21 is provided here with pads 58 and 59, which extend over the entire length of the bottle neck 21 and are pressed together firmly by the clamping means 23 and 24 in the closed position (FIG. 11). The pads 58, 59 taper greatly on their sides, so that air channels are formed at their sides in the wide open state of the bottle neck 21 (FIG. 10).

The bottle neck 21 can be brought by means of the clamping means 23 and 40 into the states "bottle neck 21 wide open for filling (FIG. 7)," "bottle neck 21 firmly closed (FIGS. 9 and 11)" and "bottle neck 21 in the resting position (FIGS. 8 and 10)."

While specific embodiments of the invention have been shown and described in detail to illustrate the application of the principles of the invention, it will be understood that the invention may be embodied otherwise without departing from such principles.

What is claimed is:

1. A rubber bottle, comprising:
    a bottle body;
    a long tube forming a stiff bottle neck with a free end and a bottle body end wherein said bottle body end is integrally connected to said bottle body, wherein said bottle neck has an inside surface with a length and a bottle neck interior space with ribs arranged on said inside surface of said bottle neck over said length of said bottle neck for making said bottle neck stiffer than said bottle body, said ribs completely fill said bottle neck interior space when said filling opening is in said closed position;
    a filling opening at said free end of said bottle neck for filling in a hot or cold liquid, especially water, wherein said filling opening has a closed position and an open position; and
    a bottle neck closure for closing said filling opening, said bottle neck having a length, such that when said filling opening is in said closed position, said bottle neck closure is located at a spaced location from said bottle body whereby said bottle neck closure is not located under a user's body during use of said rubber bottle.

2. A rubber bottle in accordance with claim 1 wherein said bottle neck closure comprises:
    a clamping means to apply a closing pressure in a closing pressure direction for closing said bottle neck filling opening with two corresponding clamping jaws between which said bottle neck filling opening can be clamped, is arranged on said bottle neck, wherein said clamping jaws form a grip for grasping said rubber bottle during filling when said filling opening is in said open position.

3. A rubber bottle in accordance with claim 2 further comprising:
    a means by which said clamping means is detachably fastened to said bottle neck.

4. A rubber bottle in accordance with claim 3 further comprising:
    one or more holding straps on said bottle neck for detachable fastening of said clamping means to said bottle neck.

5. A rubber bottle in accordance with claim 4, further comprising:
    a spread out position of said clamping means by which a force for opening said filling opening is applied to said bottle neck during filling with said clamping means in said spread out position, wherein said clamping means is held on said bottle neck by said holding straps such that said bottle neck opens when said clamping means are in said spread-out position.

6. A rubber bottle in accordance with claim 4 further comprising:
    an opened position of said clamping means; and
    a pressure directed at right angles to said closing pressure direction, applied to said bottle neck in said opened position of said clamping means such that said bottle neck opens for filling with said clamping means in said opened position.

7. A rubber bottle in accordance with claim 3, further comprising:
    a spread out position of said clamping means by which a force for opening said filling opening is applied to said bottle neck during filling with said clamping means in said spread out position, wherein said clamping means is held on said bottle neck by holding straps such that said bottle neck opens when said clamping means are in said spread-out position.

8. A rubber bottle in accordance with claim 3 further comprising:
    an opened position of said clamping means; and
    a pressure directed at right angles to said closing pressure direction, applied to said bottle neck in said opened position of said clamping means such that said bottle neck opens for filling with said clamping means in said opened position.

9. A rubber bottle in accordance with claim 2 further comprising:
    a spread out position of said clamping means by which a force for opening said filling opening is applied to said bottle neck during filling with said clamping means in said spread out position, wherein said clamping means is held on said bottle neck by holding straps such that said bottle neck opens when said clamping means are in said spread-out position.

10. A rubber bottle in accordance with claim 9, wherein: said clamping means has tongues, that can be inserted into said holding straps for attaching said clamping means to said bottle neck.

11. A rubber bottle in accordance with claim 2 further comprising:

an opened position of said clamping means; and a pressure directed at right angles to said closing pressure direction, applied to said bottle neck in said opened position of said clamping means such that said bottle neck opens for filling with said clamping means in said opened position.

12. A rubber bottle in accordance with claim 1, wherein: said ribs are longitudinal ribs that form channels for air to escape from said bottle body during filling.

13. A rubber bottle in accordance with claim 1, wherein: said filling opening has the shape of a funnel.

14. A rubber bottle comprising:

a bottle body;

a long tube forming a bottle neck with a free end and a bottle body end wherein said bottle body end is integrally connected to said bottle body;

a filling opening at said free end of said bottle neck for filling in a hot or cold liquid, especially water, wherein said filling opening has a closed position and an open position; and a bottle neck closure for closing said filling opening, said bottle neck having a length, such that when said filling opening is in said closed position, said bottle neck closure is located at a spaced location from said bottle body whereby said bottle neck closure is not located under a user's body during use of said rubber bottle, wherein:

said bottle neck closure has a clamping position;

said bottle neck has a bottle neck axis;

said closure applies a squeezing force to said bottle neck when in said clamping position in a squeezing force direction;

said bottle neck, when said bottle neck opening is in said closed position, has a minor dimension thickness measured substantially parallel to said direction of said squeezing force applied by said closure; and said minor dimension thickness is greater near said bottle neck axis than at a distance substantially perpendicularly away from said bottle neck axis.

15. A rubber bottle, comprising:

a bottle body;

a long tube forming a bottle neck with a free end and a bottle body end wherein said bottle body end is integrally connected to said bottle body;

a filling opening at said free end of said bottle neck for filling in a hot or cold liquid, especially water, wherein said filling opening has a closed position and an open position;

a bottle neck closure for closing said filling opening, said bottle neck having a length, such that when said filling opening is in said closed position, said bottle neck closure is located at a spaced location from said bottle body whereby said bottle neck closure is not located under a user's body during use of said rubber bottle;

an inside surface of said bottle neck;

a bottle neck interior space; and ribs arranged on said inside surface of said bottle neck, over said length of said bottle neck, that correspond to one another, whereby they completely fill said bottle neck interior space when said filling opening is in said closed position.

* * * * *